United States Patent [19]
Furuya et al.

[11] Patent Number: 6,087,503
[45] Date of Patent: Jul. 11, 2000

[54] QUINOLINE DERIVATIVES, THEIR PRODUCTION AND USE

[75] Inventors: Shuichi Furuya; Nobuo Choh; Satoshi Sasaki, all of Tsukuba, Japan

[73] Assignee: Takeda Chemical Industries Ltd., Osaka, Japan

[21] Appl. No.: 09/152,514

[22] Filed: Sep. 14, 1998

Related U.S. Application Data

[62] Division of application No. 08/779,609, Jan. 7, 1997, which is a continuation of application No. PCT/JP96/03019, Oct. 18, 1996.

[30] Foreign Application Priority Data

Oct. 19, 1995 [JP] Japan ................................. 7-271640

[51] Int. Cl.$^7$ ................................................. C07D 215/56
[52] U.S. Cl. ............................................................. 546/156
[58] Field of Search ............................................. 546/156

[56] References Cited

U.S. PATENT DOCUMENTS

| | | | |
|---|---|---|---|
| 4,659,691 | 4/1987 | Baasner et al. | 277/1 |
| 5,140,009 | 8/1992 | Haviv et al. | 514/16 |
| 5,171,835 | 12/1992 | Janaky et al. | 530/313 |

FOREIGN PATENT DOCUMENTS

| | | |
|---|---|---|
| 54-088276 | 7/1979 | Japan . |
| 61-191698 | 8/1986 | Japan . |
| 94/20460 | 9/1994 | WIPO . |
| 95/28405 | 10/1995 | WIPO . |

OTHER PUBLICATIONS

P. M. Gilis et al., "Synthesis and Antibacterial Evaluation of 4,7–dihydro–4–oxothieno[2,3–b] pyridine–5–carboxlyic acids", Eur. J. Med. Chem., No. 3, 1978, pp. 265–269.

R. J. Bienstock et al., "Conformational Analysis of a Highly Potent Dicyclic Gonadotropin–Releasing Hormone Antagonist by Nuclear Magnetic Resonance and Molecular Dynamics", J. Med. Chem. vol. 36, (1993), pp. 3265–3273.

Seirigaku 2, Bunkodo, (1986), pp. 610–618., {English abstract}.

Receptor Kiso to Risho, Asakurashoten, (1993), pp. 297–304., {English abstract}.

T.H. Reissmann et al., Human Reproduction, 10(8), 1974–1981, 1995.

*Primary Examiner*—Evelyn Mei Huang
*Attorney, Agent, or Firm*—Foley & Lardner

[57] ABSTRACT

The present compounds are intermediates for the preparation of quinoline derivatives and compositions having gonadotropin-releasing hormone antagonistic activity useful as propylactics or therapeutic agent for the prevention or treatment of several hormone dependent diseases, for example, a sex hormone dependent cancer (e.g. prostatic cancer, uterine or cervical cancer, breast cancer, pituitary adenoma), benign prostatic hypertrophy, myoma of the uterus, endometriosis, precocious puberty, amenorrhea, premenstrual syndrome, polycystic ovary syndrome and acne vulgaris; are effective as a fertility controlling agent in both sexes (e.g. a pregnancy controlling agent and a menstrual cycle controlling agent); can be used as a male or female contraceptive, as an ovulation-inducing agent; can be used as an infertility treating agent by using a rebound effect owing to a stoppage of administration thereof; and are useful for modulating estrous cycles in animals in the field of animal husbandry, as agents for improving the quality of edible meat or promoting the growth of animals, and as agents for promoting spawning in fish.

3 Claims, No Drawings

QUINOLINE DERIVATIVES, THEIR PRODUCTION AND USE

This application is a divisional of application Ser. No. 08/779,609, filed Jan. 7, 1997 which is a continuation of PCT/JP96/03019, filed on Oct. 18, 1996.

TECHNICAL FIELD

The present invention relates to novel quinoline derivatives and salts thereof. The present invention further relates to methods for manufacturing these quinoline derivatives and the salts thereof, and pharmaceutical compositions containing the quinoline derivatives.

BACKGROUND ART

Secretion of anterior pituitary hormone is controlled by peripheral hormones secreted from target organs for the respective hormones and by secretion-accelerating or -inhibiting hormones from the hypothalamus, which is the upper central organ of the anterior lobe of the pituitary (in this specification, these hormones are collectively called "hypothalamic hormones"). At the present stage, nine kinds of hormones have been confirmed as hypothalamic hormones, including, for example, thyrotropin releasing hormone (TRH) or gonadotropin releasing hormone {GnRH: sometimes called LH-RH (luteinizing hormone releasing hormone)} (cf. Seirigaku 2, compiled by M. Iriku and K Toyama, published by Bunkohdo, pp.610–618, 1986). These hypothalamic hormones are assumed to show their actions via the receptor which is considered to exist in the anterior lobe of the pituitary (cf. ibid), and studies of receptor genes specific to these hormones, including those of humans, have been developed (Receptor Kiso To Rinshô, compiled by H. Imura, et al., published by Asakura Shoten, pp.297–304, 1993). Accordingly, antagonists or agonists specifically and selectively acting on these receptors control the action of hypothalamic hormone and the secretion of anterior pituitary hormone. As a result, they are expected to be useful as prophylactic and therapeutic agents of anterior pituitary hormone dependent diseases.

As compounds having GnRH antagonistic activity, a number of compounds including, for example, derivatives of GnRH such as straight-chain peptides, (U.S. Pat. No. 5,140,009 and No. 5,171,835), cyclic hexapeptide derivatives [Japanese Patent Application Laid-open No. 61(1986)-191698) or bicyclic peptide derivatives [Journal of medicinal chemistry, Vol.36, pp.3265–3273, 1993] have been disclosed.

These compounds are, however, all peptides, which leave many problems including, for example, dosage forms, stability of drugs, durability of actions and stability on metabolism. Orally administrable GnRH antagonistic drugs, especially non-peptide ones, which has therapeutic effects as for hormone-dependent cancer, e.g. prostate cancer, and for endometriosis and precocious puberty but not to cause the transient pituitary-gonadotropic action (acute action), are strongly desired.

The object of the invention lies in providing novel quinoline derivatives having excellent gonadotropic hormone releasing hormone antagonistic activity as well as being excellent gonadotropic hormone releasing hormone antagonistic agents.

DISCLOSURE OF INVENTION

Thus, the present invention provides (1) A compound of the formula:

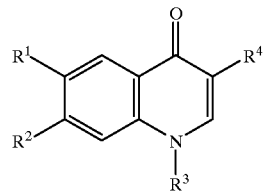

(I)

wherein $R^1$ is a group of the formula:

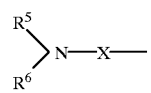

in which $R^5$ is an aralkyl group, $R^6$ is an alkyl group, X is an alkylene group, or an alkyl group which may optionally be substituted by halogen, $R^2$ is an acylaminoaryl group, $R^3$ is a halogenoaralkyl group, $R^4$ is a carboxyl group which may optionally be esterified or amidated, or a salt thereof, (2) A compound according to the item (1), wherein $R^1$ is a group of the formula:

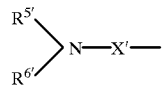

wherein $R^{5'}$ is a $C_{7-13}$ aralkyl group, $R^{6'}$ is a $C_{1-6}$ alkyl, $X'$ is a $C_{1-6}$ alkylene group, or $C_{1-6}$ alkyl group which may optionally be substituted by halogen, $R^2$ is a $C_{1-6}$ acylamino-$C_{6-14}$ aryl group, $R^3$ is a halogeno-$C_{7-13}$ aralkyl group, $R^4$ is a carboxyl group which may optionally be esterified with $C_{1-6}$ alkyl, (3) A compound according to the item (2), wherein $R^1$ is N-$C_{7-13}$ aralkyl-N-$C_{1-6}$ alkyl-aminomethyl, (4) A compound according to the item (1), wherein $R^1$ is N-benzyl-N-methylaminomethyl, $R^2$ is propionylaminophenyl, $R^3$ is difluorobenzyl, (5) 6-(N-Benzyl-N-methylaminomethyl)-1,4-dihydro-1-(2, 6-difluorobenzyl)-7-(4-propionylaminophenyl)-4-oxoquinoline-3-carboxylic acid or its salt, (6) A method for producing a compound as defined in the item (1) or its salt, which comprises reacting a compound of the formula:

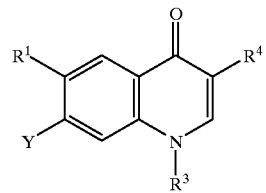

(II)

wherein Y is halogen, $R^1$ is a group of the formula

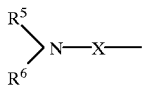

wherein $R^5$ is an aralkyl group, $R^6$ is alkyl group, X is an alkylene group, $R^3$ is a halogenoaralkyl group, $R^4$ is a carboxyl group, an ester thereof or an amido thereof, or its salt, with an aryl borric acid derivative of the formula:

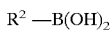

wherein $R^2$ is an acylaminoaryl group, or reacting a compound of the formula:

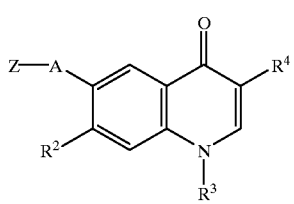

(III)

wherein Z is a leaving group, A is an alkylene group and the other groups have the same meaning as defined above, or its salt, with a compound of the formula:

wherein $R^5$ and $R^6$ have the same meaning as defined above, (7) A pharmaceutical composition, which comprises a compound as defined in the item (1) and a carrier, excipient or diluent therefor, (8) A pharmaceutical composition according to the item (7), which is for antagonizing gonadotropin-releasing hormone activity, (9) A pharmaceutical composition according to the item (8), which is a composition for treating or preventing a sex hormone dependent disease,

(10) A method for treating a mammla suffering from a gonadotropin-releasing hormone derived disorder, which comprises administering an effective amount of a compound as defined in the item (1) to the mammal, and

(11) Use of a compound as defined in the item (1) for producing a pharmaceutical composition for antagonizing gonadotropin-releasing hormone activity in a mammal suffering from a sex hormone dependent disease.

The nuclesis of the present compound, 4-oxoquinoline, is shown below:

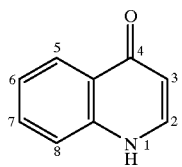

As the aralkyl group of $R^5$ in $R^1$, $C_{7-13}$ aralkyl is preferable, and the $C_{7-13}$ aralkyl is exemplified by benzyl, phenethyl, biphenylylmethyl, benzhydryl. In particular, benzyl is most preferable.

As the alkyl groups $R^6$, a $C_{1-6}$ alkyl group is preferable, and the $C_{1-6}$ alkyl group is exemplified by methyl, ethyl, n-propyl, isopropyl, n-butyl, isobutyl, s-butyl, t-butyl, n-pentyl, isopentyl, neopentyl, hexyl. Among them, $_{1-3}$ alkyl is preferable.

As the alkylene group of X in $R^1$ and A, $C_{1-6}$ alkylene is preferable, and $C_{1-6}$ alkylene is exemplified by methylene, ethylene, propylene, butylene, pentylene, hexylene. Among them, $C_{1-3}$ alkylene is more preferable.

As the alkyl group in the alkyl group which may optionally be substituted by halogen of $R^1$, it is exemplified by those mentioned above. As the halogen, mention is made of fluorine, chlorine, bromine and iodine. As the preferred alkyl group which has halogen, mention is made of bromomethyl.

As the acylaminoaryl of $R^2$, $C_{1-6}$ acyl amino-$C_{6-14}$ aryl group is preferable. As examples of the $C_{1-6}$ acyl, mention is made of formyl, acetyl, propionyl, butyryl, isobutyryl, valeryl, isovaleryl. As examples of the $C_{6-14}$ aryl, mention is made of phenyl, naphthyl, anthryl.

As the halogenoaralkyl of $R^3$, halogeno-$C_{7-19}$ aralkyl is preferable. As the halogen in the halogenoaralkyl, mention is made of fluorine, chlorine, bromine and iodine. As examples of aralkyl in the halogenoaralkyl, mention is made of benzyl, phenethyl, benzhydryl, in particular, benzyl is most preferable.

As the ester in the esterified carboxyl of $R^4$, $C_{1-6}$ alkyl ester is preferable, and examples of it are methylester, ethylester, n-propylester, isopropylester, n-butylester, isobutylester, s-butylester, t-butylester, n-pentylester, isopentylester, neopentylester, n-hexylester. Among them, ethyl ester is most preferable.

The amidated carboxyl of $R^4$ is exemplified by carbamoyl, methylcarbamoyl, 2-pyridylcarbamoyl, benzylcarbamoyl, isopropylcarbamoyl.

As the more preferable groups in the compound [I], $R^1$ is N-benzyl-N-methylaminomethyl, $R^2$ is propionylaminophenyl or isobutyrylaminophenyl, $R^3$ is difluorobenzyl, and $R^4$ is ethoxycarbonyl.

Furthermore, the present invention provides a quinoline derivative (X) of the formula (X):

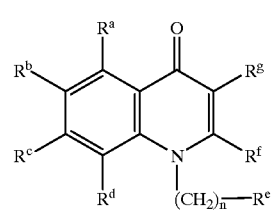

(X)

wherein each of $R^a$, $R^b$, $R^c$, $R^d$, $R^f$ and $R^g$ are hydrogen or a group bonded through a carbon atom, a nitrogen atom, an oxygen atom or a sulfur atom, $R^a$ denotes an optionally substituted homo- or heterocyclic group, with the proviso that all of $R^a$, $R^b$, $R^c$, $R^d$, $R^f$ and $R^g$ are not hydrogen atoms at the same time, which has a gonadotropic hormone releasing hormone antagonistic activity.

The group bonded through a carbon atom in the compound (X) includes, for example, (1) a hydrocarbon residue, (2) an acyl group, (3) an carbamoyl group, and (4) a heterocyclic group which bonds through carbon atom of the heterocyclic group. Each of these groups may optionally be substituted. Furthermore, as the group bonded through a carbon atom, (5) a carboxyl group or, an ester or amide thereof, (6) a cyano group, is mentioned.

The ester of carboxyl group includes a group of the formula: —COO—$R^{11}$, wherein $R^{11}$ is a hydrogen atom, a hydrocarbon residue or a heterocyclic group. Each of these hydrocarbon residue and heterocyclic group may optionally be substituted.

The amide of carboxyl group includes a group of the formula; —CO—$NR^{12}R^{13}$, wherein $R^{12}$ is a hydrogen atom, a hydrocarbon residue or an heterocyclic group or a group bonded through a sulfur atom. $R^{13}$ represents a hydrogen atom or a hydrocarbon residue. $R^{12}$ and $R^{13}$ may form a 5 to 7 membered cyclic amino group together with the neighboring nitrogen atom or a nitrogen-containing heterocyclic group together with a neighboring nitrogen atom. Each of these hydrocarbon residue, heterocyclic group, cyclic amino group, nitrogen-containing heterocyclic group may optionally be substituted.

Examples of the group bonded through nitrogen atom in the compound (X), (1) a nitro group, (2) a group of the formula: —$NR^{14}R^{15}$, wherein $R^{14}$ represents a hydrogen atom, a hydrocarbon residue, a hydrocarbon residue-oxy group, an acyl group, a hydroxyl group, a heterocyclic group, a group of the formula: —$SO_P$—$R^{16}$, wherein p denotes an integer of 1 or 2, $R^{16}$ represents a hydrocarbon residue; and $R^{15}$ represents a hydrogen atom or a hydrocarbon residue, and the group —NR $R^{1415}$ may form a cyclic amino group. Each of these hydrocarbon residue, hydrocarbon residue-oxy group, acyl group, hydroxyl group, heterocyclic group and cyclic amino group may optionally be substituted.

Examples of the group bonded through an oxygen atom in the compound (X) include a group of the formula: —O—$R^{17}$, wherein $R^{17}$ is a hydrogen atom, a hydrocarbon residue, an acyl group or a heterocyclic group. Each of these hydrocarbon residue, acyl group and heterocyclic group may optionally substituted. Examples of the group bonded through a sulfur atom in the compound (X) include a group of the formula: —$S(O)_t$—$R^{18}$, wherein $R^{18}$ is a hydrogen atom, a hydrocarbon residue or a heterocyclic group, and t denotes an integer of 0 to 2. Each of these hydrocarbon residue and heterocyclic group may be optionally substituted.

The hydrocarbon residue in the hydrocarbon residue which may be optionally substituted and the hydrocarbon residue-oxy group which may optionally be substituted, described above includes a hydrocarbon residue having one to 20 carbon atoms. As examples of the $C_{1-20}$ hydrocarbon residue, mention is made of (1) $C_{1-15}$ alkyl, e.g. methyl, ethyl, n-propyl, isopropyl, n-butyl, isobutyl, sec-butyl, t-butyl, pentyl, hexyl, heptyl, octyl, nonyl, decyl, undecyl, dodecyl, tridecyl, tetradecyl, pendadecyl, etc, and among others, with $C_{1-10}$ alkyl or $C_{1-6}$ alkyl being preferable; (2) $C_{3-10}$ cycloalkyl, e.g. cyclopropyl, cyclobutyl, cyclopentyl, cyclohexyl, cycloheptyl, cyclooctyl, cyclononyl, etc, and among others, with $C_{3-6}$ cycloalkyl being preferable; (3) $C_{2-10}$ alkenyl, e.g. vinyl, allyl, isopropenyl, 1-butenyl, 2-butenyl, 3-butenyl, 2-methylallyl, butadienyl, hexatrienyl, 3-octenyl, etc, and among others, with $C_{1-10}$ alkyl or $C_{2-6}$ alkenyl being preferable, (4) $C_{2-10}$ alkylyl, e.g. ethynyl, 2-propynyl, isopropynyl, buthynyl, t-buthynyl, 3-hexynyl, etc, and among others, with $C_{2-6}$ alkynyl being preferable; (5) $C_{3-10}$ cycloalkenyl, e.g. cyclopropenyl, cyclopentenyl, cyclohexenyl, etc, among others, with $C_{3-6}$ cycloalkenyl being preferable; (6) $C_{6-14}$ aryl e.g. phenyl, 1- or 2naphthyl, anthryl, phenanthryl, acenaphthyl, anthracenyl, etc., among others, with phenyl and naphthyl being preferable; and (7) $C_{7-20}$ aralkyl, e.g. benzyl, phenethyl, benzhydryl, trityl, etc, and among others, with benzyl and phenethyl being preferable.

The substituents which said hydrocarbon residue may optionally have include (1) halogen, (2) nitro, (3) nitroso, (4) cyano, (5) hydroxyl group which may optionally be substituted by (i) $C_{1-6}$ alkyl, which may optionally be substituted by hydroxyl, $C_{1-6}$ alkoxy, $C_{1-3}$ alkoxy-$C_{1-3}$ alkoxy, $C_{1-3}$ alkylthio, hydroxy-$C_{1-3}$ alkoxy, $C_{1-6}$ alkyl-carbonyl, carboxyl, carbamoyl, $C_{16}$ alkyl-carbamoyl, 5 to 7 membered nitrogen containing heterocyclic group or halogen, (ii) $C_{1-4}$ acyl, (iii) $C_{7-20}$ arakyl, which may optionally be substituted by halogen, $C_{1-3}$ alkoxy or $C_{1-4}$ alkyl, (iv) $C_{6-14}$ aryl, which may optionally be substituted by halogen, (v) $C_{2-6}$ alkenyl, (vi) $C_{3-7}$ cycloalkyl, (vii) $C_{13}$ alkoxy-carbonyl, (viii) mono- or di-$C_{1-6}$ alkyl-amino, (ix) $C_{2-6}$ alkenyl-amino, (x) $C_{1-3}$ alkoxy-carbonyl, (xi) $C_{1-6}$ alkyl-carbonyl, (xii) $C_{3-6}$ cycloalkyl-oxycarbonyl or (xiii) trifluorosulfonyl, (6) a group of the formula: —$S(O)f$-$R^{21}$, wherein f is an integer of 0 to 2, $R^{21}$ represents a hydrogen atom or a hydrocarbon residue which may optionally be substituted, the hydrocarbon residue has the same meaning as defined above, among others, $C_{1-20}$ alkyl especially $C_{1-6}$ alkyl, $C_{6-14}$ aryl, $C_{7-20}$ aralkyl are preferable, and as examples of the substituent to the hydrocarbon residue, mention is made of halogen, nitro, cyano, hydroxy, oxo, thioxo, carboxyl, cyano-$C_{6-14}$ aryl, halogeno-$C_{6-14}$ aryl, etc, (7) an optionally substituted amino group, which is represented by the formula: —$NR^{22}R^{23}$, wherein each of $R^{22}$ and $R^{23}$ are hydrogen, $C_{1-6}$ alkyl, $C_{1-6}$ acyl or a 5 to 8 membered heterocyclic group which is mentioned above or a group bonded through nitrogen atom as described above, (8) a group of the formula: —CO—$R^{24}$ wherein $R^{24}$ denotes (i) hydrogen, (ii) hydroxyl, (iii) $C_{1-10}$ alkyl, (iv) $C_{1-6}$ alkoxy which may be substituted with $C_{6-14}$ aryl which may optionally be substituted with halogen or nitro, (v) $C_{3-6}$ cycloalkyl, (vi) $C_{6-14}$ aryl, (vii) $C_{6-14}$ aryloxy, (Viii) $C_{7-20}$ aralkyl, (ix) an optionally substituted amino group which is defined (7) above or (x) an optionally substituted 5- to 8-membered heterocyclic group which is mentioned below, expecially, $C_{1-10}$ acyl is preferable, (9) a 5- through 8-membered heterocyclic group containing 1–4 hetero-atom(s) selected from oxygen (O), sulfur (S) and nitrogen (N) as ring members, the heterocyclic group being optionally substituted by (i) halogen, (ii) $C_{1-4}$ alkyl, (iii) $C_{1-3}$ alkoxy, (iv) $C_{1-4}$ alkylthio, (v) phenoxy which may optionally be substituted by a halogen, (10) sulfo, (11) $C_{6-14}$ aryl, e.g. phenyl, naphthyl, anthryl, phenanthryl, acenaphthyl, anthracenyl, etc, which may optionally be substituted with one to 4 of (a) hydroxyl, (b) amino, (c) mono- or di-$C_{1-6}$ alkylamino, e.g. methylamino, ethylamino, propylamino, dimethylamino, diethylamino, etc, (d) $C_{1-6}$ alkoxy, e.g. methoxy, ethoxy, propoxy, hexyloxy, etc or (e) halogen, (12) $C_{3-7}$ cycloalkyl, (13) $C_{1-6}$ alkylenedioxy, e.g. methylenedioxy, ethylenedioxy, propylenedioxy, 2,2-dimethylenedioxy, etc, (14) oxo, (15) thioxo, (16) $C_{2-6}$ alkynyl, (17) $C_{3-10}$ cycloalkyl, (18) $C_{2-10}$ alkenyl, e.g. vinyl, allyl, isopropenyl, 1-butenyl, 2-butenyl, butadienyl, hexatrienyl, etc., and among others, $C_{2-6}$ alkenyl is preferable, (19) $C_{7-20}$ aralkyl, which has the same meaning as defined above, (21) amidino, and (22) azido.

The above substituents may further have substituents. Such substituents includes (1) hydroxy, (2) amino, (3) mono- or di-$C_{1-4}$ alkyl-amino (e.g. methylamino, ethylamino, propylamino, dimethylamino, diethylamino, etc), (4) $C_{1-4}$ alkoxy (e.g. methoxy, ethoxy, propoxy, etc), (5) halogen and (6) nitro. The number of the substituents is preferably 1 to 4, and more preferably 1 to 2.

When the above optionally substituted hydrocarbon residue is cycloalkyl, cycloalkenyl, aryl or aralkyl, each of the group may have one to three of $C_{1-6}$ alkyl, e.g. methyl, ethyl, propyl, isopropyl, butyl, as a substituent. The $C_{1-6}$ alkyl group may further substituted by one to three of hydroxy, oxo, $C_{1-3}$ alkoxy, e.g. methoxy, ethoxy, n-propoxy, isopropoxy, $C_{1-3}$ alkylthio, halogen or carbamoyl.

As examples of the substituted alkyl, mention is made of (1) formyl, i.e. methyl is substituted by oxo, (2) carboxyl, i.e. methyl is substituted by oxo and hydroxy, (3) $C_{1-6}$ alkoxy-carbonyl, i.e. methyl is substituted by oxo and alkoxy, e.g. methoxycarbonyl, ethoxycarbonyl, t-butoxycarbonyl, (4) hydroxy-$C_{1-6}$ alkyl, e.g. hydroxymethyl, hydroxyethyl, hydroxypropyl, hydroxybutyl, (5) $C_{1-3}$ alkoxy-$C_{1-6}$ alkyl, e.g. methoxymethyl, ethoxyethyl, ethoxybutyl, propoxymethyl, propoxyhexyl.

In the above optionally substituted hydrocarbon residue, the number of the substituent(s) is preferably 1 to 6, more preferably 1 to 5, still more preferably 1 to 3 and most preferably 1 to 2. The number of the substituent(s) which is substituted on the substituent is preferably 1 to 3, more preferably 1 or 2.

As the acyl group in the optionally substituted acyl group, mention is made of an acyl group which is derived from $C_{1-24}$ aliphatic carboxylic acid.

Further examples of the acyl group include formyl, $C_{1-6}$ alkyl-carbonyl (e.g. acetyl, ethylcarbonyl, propylcarbonyl, tert-propylcarbonyl), $C_{1-6}$ alkoxycarbonyl (e.g. methoxycarbonyl, ethoxycarbonyl, t-butoxycarbonyl), $C_{6-14}$ aryl-carbonyl (e.g. benzoyl), $C_{6-14}$ aryloxy-carbonyl (e.g. phenoxycarbonyl), $C_{7-15}$ aralkyl-carbonyl (e.g. benzylcarbonyl), and $C_{7-19}$ aralkyloxy-carbonyl (e.g. benzyloxy carbonyl). Among others, $C_{1-10}$ acyl is preferable. As substituents in the optionally substituted acyl, mention is made of those in the optionally substituted hydrocarbon residue. The substituents on the $C_{1-10}$ acyl group are the same as those on the hydrocarbon residue.

Examples of the optionally substituted carbamoyl group include a carbamoyl group which may optionally be substituted by a $C_{1-20}$ hydrocarbon residue. As the $C_{1-20}$ hydrocarbon residue, mention is made of those described hereinbefore. Concrete examples of the substituted carbamoyl include mono- or di-$C_{1-15}$ alkyl-carbamoyl, e.g. methylcarbamoyl, ethylcarbamoyl, hexylcarbamoyl, dimethylcarbamoyl, methylethylcarbamoyl. The substituents on the carbamoyl group are the same as those on the hydrocarbon residue.

As the heterocyclic group in the optionally substituted heterocyclic group which bonds with the constitutive carbon atom, mention are made of 5 to 8 membered heterocyclic groups which have one to 4 hetero atoms selected from an oxygen atom, sulfur atom and nitrogen atom than carbon atom; and two ring or three ring condensed-ring heterocyclic groups composed of the above heterocyclic group and other ring groups.

Examples of the heterocyclic ring groups include (1) 5-membered cyclic groups containing, besides the carbon atom, 1 to 4 hetero-atoms selected from oxygen atom, sulfur atom and nitrogen atom, such as thienyl, furyl, pyrrolyl, pyrrolinyl, oxazolyl, thiazolyl, pyrazolyl, imidazolyl, imidozolinyl, isoxazolyl, isothiazolyl, 1,2,4-oxadiazolyl, 1,3,4-oxadiazolyl, furazanyl, 1,2,4-thiadiazolyl, 1,2,3-thiadiazolyl, 1,2,5-thiadiazolyl, 1,2,3-triazolyl, 1,2,4-triazolyl, triazinyl, triazolidinyl, and 1H- or 2H-tetrazolyl; (2) 6-membered cyclic groups containing, besides, carbon atom, 1 to 4 hetero-atoms selected from an oxygen atom, sulfur atom and nitrogen atom, as exemplified by pyridyl, pyrimidinyl, thiomorpholinyl, morpholinyl, triazinyl, pyrrolidinyl, piperazinyl, piperidinyl, pyranyl, thiopyranyl, 1,4-oxadinyl, 1,4-thiazinyl, 1,3-thiazinyl, triazinyl, oxotriazinyl, pyridazinyl and pyrazinyl. (3) bicyclic or tricyclic condensed ring groups containing, besides carbon atom, 1 to 4 heteroatoms selected from oxygen atom, sulfur atom and nitrogen atom, as exemplified by benzofuryl, benzothiazolyl, benzoxazolyl, tetrazolo[1,5-b]pyridazinyl, triazolo(4,5-b]pyridazinyl, benzoimidazolyl, quinolyl, isoquinolyl, cinnolinyl, phthaladinyl, quinazolinyl, quinoxalinyl, indolidinyl, indolyl, quinolidinyl, 1,8-naphthylidinyl, purinyl, pteridinyl, dibenzofuranyl, carbazolyl, acridinyl, phenanthridinyl, chromanyl, benzoxadinyl, phenazinyl, phenothiazinyl and phenoxazinyl.

Examples of the substituents, which the heterocyclic group may have include (1) $C_{1-6}$ alkyl, (2) $C_{2-6}$ alkenyl, (3) $C_{2-6}$ alkynyl, (4) $C_{3-6}$ cycloalkyl, (5) $C_{5-7}$ cycloalkenyl, (6) $C_{7-11}$ aralkyl, (7) $C_{6-14}$ aryl, (8) $C_{1-6}$ alkoxy, (9) $C_{6-14}$ aryloxy (e.g. phenoxy), (10) $C_{1-6}$ alkanoyl, e.g. formyl, acetyl, propionyl, n-butyryl and isobutyryl, (11) $C_{6-14}$ arylcarbonyl, e.g. benzoyl, (12) $C_{1-6}$ alkanoyloxy, e.g. formyloxy, acetyloxy, propionyloxy, n-butyryloxy and isobutyryloxy, (13) $C_{6-14}$ aryl-carbonyloxy, e.g. benzoyloxy, (14) carboxyl, (15) $C_{1-6}$ alkoxy-carbonyl, e.g. methoxycarbonyl, ethoxycarbonyl, n-propoxycarbonyl, isopropoxycarbonyl, n-butoxycarbonyl, isobutoxycarbonyl and tert-butoxycarbonyl, (16) carbamoyl, (17) N-mono-$C_{1-4}$ alkylcarbamoyl, e.g. N-methylcarbamoyl, N-ethylcarbamoyl, N-propylcarbamoyl, N-isopropylcarbamoyl and N-butylcarbamoyl, (18) N,N-di-$C_{1-4}$ alkylcarbamoyl, e.g. N,N-dimethylcarbamoyl, N,N-diethylcarbamoyl, N,N-dipropylcarbamoyl and N,N-dibutylcarbamoyl, (19) cyclic aminocarbonyl, e.g. 1-aziridinylcarbonyl, 1-azetidinylcarbonyl, 1-pyrrolidinylcarbonyl, 1-piperidinylcarbonyl, N-methylpiperazinylcarbonyl and morpholinocarbonyl, (20) halogen, (21) mono- or tri-halogeno-$C_{1-4}$ alkyl, e.g. chloromethyl, dichloromethyl, trifluoromethyl and trifluoroethyl, (22) oxo, (23) amidino, (24) imino, (25) amino, (26) mono- or di $C_{1-4}$ alkylamino, e.g. methylamino, ethylamino, propylamino, isopropylamino, butylamino, dimethylamino, diethylamino, dipropylamino, diisopropylamino and dibutylamino, (27) 3- to 6-membered cyclic amino group containing, besides the carbon atom and one nitrogen atom, 1 to 3 hetero-atoms selected from oxygen atom, sulfur atom and nitrogen atom, e.g. aziridinyl, azetidinyl, pyrrolidinyl, pyrrolinyl, pyrrolyl, imidazolyl, pyrazolyl, imidazolidinyl, piperidino, morpholino, dihydropyridyl, N-methylpiperazinyl and N-ethylpiperazinyl, (28) $C_{1-6}$ alkanoylamino, e.g. formamido, acetamido, trifluoroacetamido, propionylamido, butyrylamido and isobutyrylamido, (29) benzamido, (30) carbamoylamino, (31) N-$C_{1-4}$ alkylcarbamoylamino, e.g. N-methylcarbamoylamino, N-ethylcarbamoylamino, N-propylcarbamoylamino, N-isopropylcarbamoylamino and N-butylcarbamoylamino, (32) N,N-di-$C_{1-4}$ alkylcarbamoylamino, e.g. N,N-dimethylcarbamoylamino, N,N-diethylcarbamoylamino, N,N-dipropylcarbamoylamino and N,N-dibutylcarbamoylamino, (33) $C_{1-3}$ alkylenedioxy, e.g. methylenedioxy and ethylenedioxy, (34) —B(OH)$_2$, (35) hydroxyl, (36) epoxy (—O—), (37) nitro, (38) cyano, (39) mercapto, (40) sulfo, (41) sulfino, (42) phosphono, (43) dihydroxyboryl, (44) sulfamoyl, (45) $C_{1-6}$ alkylsulfamoyl, e.g. N-methylsulfamoyl, N-ethylsulfamoyl, N-propylsulfamoyl, N-isopropylsulfamoyl and N-butylsulfamoyl, (46) di-$C_{1-6}$ alkylsulfamoyl, e.g. N,N-dimethylsulfamoyl, N,N-diethylsulfamoyl, N,N-dipropylsulfamoyl and N,N-dibutylsulfamoyl, (47) $C_{1-6}$ alkylthio, e.g. methylthio, ethylthio, propylthio, isopropylthio, n-butylthio, sec-butylthio and tert-butylthio, (48) phenylthio, (49) $C_{1-6}$ alkylsulfinyl, e.g. methylsulfinyl, ethylsulfinyl, propylsulfinyl and butylsulfinyl, (50) phenylsulfinyl, (51) $C_{1-6}$ alkylsulfonyl, e.g. methylsulfonyl, ethylsulfonyl, propylsulfonyl and butylsulfonyl, and (52) phenylsulfonyl. The number of the substituents ranges from 1 to 6, preferably 1 to 3.

Examples of the above-mentioned optionally substituted heterocyclic groups which bind through a carbon atom include 5- to 8-membered cyclic groups or condensed ring thereof containing, besides carbon atom, 1 to 4 hetero-atoms such as oxygen atom, sulfur atom and nitrogen atom. Examples of 5-membered cyclic groups containing, besides carbon atom, 1 to 4 hetero-atoms selected from oxygen atom, sulfur atom and nitrogen atom which bond through a carbon atom include 2- or 3-thienyl, 2- or 3-furyl, 2- or 3-pyrrolyl, 2-, 4- or 5-oxazolyl, 2-, 4- or 5-thiazolyl, 3-, 4- or 5-pyrazolyl, 2-, 3-pyrrolidinyl, 2-, 4- or 5-imidazolyl, 2-imidazolidinyl, 3,4- or 5-isoxazolyl, 3-, 4- or 5-isothiazolyl, 3- or 5-(1,2,4-oxadiazolyl), 2-, 5- or 6-(1,3,4-oxadiazolyl), 3- or 5-(1,2,4-thiadiazolyl), 2- or 5-(1,3,4-thiadiazolyl), 4- or 5-(1,2,3-thiadiazolyl), 3- or 4-(1,2,5-thiadiazolyl), 2- or 5-(1,2,3-triazolyl), 3- or 5-(1,2,4-triazolyl), and 5-(1H or 2H-tetrazolyl). Examples of 6-membered cyclic groups containing, besides, carbon atom, 1 to 4 heteroatoms selected from oxygen atom, sulfur atom or nitrogen atom which bind through a carbon atom include 2-, 3- or 4-pyridyl, 2-, 4- or 5-pyrimidinyl, 2- or 3-thiomorpholinyl, 2- or 3-morpholinyl, 3- or 6-triazinyl, 2-, 3- or 4-piperidinyl, 2- or 3-piperazinyl, 2- or 3-pyranyl, 2- or 3-thiopyranyl, 2- or 3-(1,4-oxadinyl), 2- or 3-(1,4-thiazinyl), 1- or 4-(1,3-thiazinyl), 3- or 6-triazinyl, 3- or 4-pyridazinyl, 2- or 3-pyrazinyl and 3- or 4-pyridazinyl. Examples of bicyclic or tricyclic condensed ring groups containing, besides carbon atom, 1 to 4 hetero-atoms selected from oxygen atom, sulfur atom and nitrogen atom which binds through a carbon atom include benzofuryl, benzothiazolyl, benzoxazolyl, tetrazolo[1,5-b]pyridazinyl, triazolo[4,5-b]pyridazinyl, benzoimidazolyl, quinolyl, isoquinolyl, cinnolinyl, phthaladinyl, quinazolinyl, quinoxalinyl, indolidinyl, indolyl, quinolidinyl, 1,8-naphthylidinyl, purinyl, pteridinyl, dibenzofuranyl, carbazolyl, acridinyl, phenathridinyl, chromanyl, benzoxadinyl, phenazinyl, phenothiazinyl and phenoxazinyl. The substituents on the heterocyclic groups which bond through a carbon atom are the same as those on the heterocyclic group above-mentioned.

As examples of the 5 to 7 membered cyclic amino groups containing nitrogen atom, i.e. cyclic amino group or nitrogen atom-containing heterocyclic group, mention is made of pyrrolidinyl, pyrrolinyl, pyrrolyl, pyrazolidinyl, pyrazolinyl, pyrazolyl, imidazolidinyl, imidazolinyl, imidazolyl, 1,2,3-triazinyl, 1,2,3-triazolidinyl, 1,2,3-triazolyl, 1,2,3,4-tetrazolyl, piperidinyl, piperazinyl, azepinyl, hexamethyleneamino, oxazolidino, morpholino, thiazolidino or thiomorpholino. As more preferable cyclic amino groups, mention is made of pyrolidinyl, pyrazolinyl, pyrazolyl, piperidinyl, piperazinyl, morpholino and thiomorpholino.

The cyclic amino groups may be substituted. The examples of the substituents includes (1) $C_{1-6}$ alkyl, (2) $C_{6-14}$ aryl, (3) $C_{7-10}$ aralkyl, (4) benzhydryl, (5) $C_{1-6}$ alkyl-carbonyl, (6) $C_{6-14}$ aryl-carbonyl, (7) $C_{1-6}$ alkoxy-carbonyl. As the preferable substituent, mention is made of $C_{1-6}$ alkyl, preferably $C_{1-3}$ alkyl.

Examples of the homocyclic group in the optionally substituted homocyclic groups include 3- to 7-membered cyclic hydrocarbon groups consisting of only carbon atoms, for example, $C_{6-10}$ aryl, e.g. phenyl, naphthyl; $C_{3-7}$ cycloalkyl, e.g. cyclopropyl, cyclobutyl, cyclopentyl, cyclohexyl and cycloheptyl; and $C_{3-7}$ cycloalkenyl, e.g. cyclopropenyl, cyclobutenyl, cyclopentenyl, cyclohexenyl and cycloheptenyl.

Examples of the substituents which the said homocyclic groups may have, include (1) $C_{1-15}$ alkyl and, among others, $C_{1-6}$ alkyl being preferable which may optionally be substituted by a halogen, (2) $C_{3-10}$ cycloalkyl, (3) $C_{2-10}$ alkenyl, (4) $C_{2-10}$ alkynyl, (5) $C_{3-10}$ cycloalkyl, (6) $C_{6-10}$ aryl, (7) $C_{7-20}$ aralkyl, (8) nitro, (9) hydroxyl, (10) mercapto, (11) oxo, (12) thioxo, (13) cyano, (14) carbamoyl, (15) carboxyl, (16) $C_{1-6}$ alkoxy-carbonyl, e.g. methoxycarbonyl and ethoxycarbonyl, (17) sulfo, (18) halogen, (19) $C_{1-6}$ alkoxy, (20) $C_{6-10}$ aryloxy, e.g. phenoxy, (21) $C_{1-6}$ acyloxy, e.g. acetoxy, propionyloxy, (22) $C_{1-6}$ alkylthio, e.g. methylthio, ethylthio, n-propylthio, isopropylthio, n-butylthio and t-butylthio, (23) $C_{6-10}$ arylthio, e.g. phenylthio, (24) $C_{1-6}$ alkylsulfinyl, e.g. methylsulfinyl and ethylsulfinyl, (25) $C_{6-10}$ arylsulfinyl, e.g. phenylsulfinyl, (26) $C_{1-6}$ alkylsulfonyl, e.g. methylsulfonyl and ethylsulfonyl, (27) $C_{6-10}$ arylsulfonyl, e.g. phenylsulfonyl, (28) amino, (29) $C_{1-6}$ acylamino, e.g. acetylamino and propylamino, (30) mono- or di- $C_{1-4}$ alkylamino, e.g. methylamino, ethylamino, n-propylamino, isopropylamino, n-butylamino, dimethylamino and diethylamino, (31) $C_{3-8}$ cycloalkylamino, e.g. cyclopropylamino, cyclobutylamino, cyclopentylamino and cyclohexylamino, (32) $C_{6-10}$ arylamino, e.g. anilino, (33) $C_{1-6}$ alkanoyl, e.g. formyl, acetyl and hexanoyl, (34) $C_{1-6}$ alkanoyloxy, e.g. acetoxy, propionyloxy, (35) $C_{6-10}$ aryl-carbonyl, e.g. benzoyl, and (36) 5- to 6-membered heterocyclic group containing, besides carbon atom, 1 to 4 hetero-atoms selected from oxygen, sulfur and nitrogen, e.g. 2- or 3-thienyl, 2- or 3-furyl, 3-, 4- or 5-pyrazolyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1H or 2H-tetrazolyl, 2-, 3- or 4-pyridyl, 2-, 4- or 5-pyrimidyl, 3- or 4-pyridazinyl, quinolyl, isoquinolyl and indolyl. The number of substituents ranges from 1 to 6, preferably from 1 to 3, more preferably from 1 to 2.

In the compound (X), as preferred group bonded through a carbon atom, mention is made of an optionally substituted $C_{1-20}$ hydrocarbon residue, especially, an optionally substituted $C_{1-10}$ alkyl group, an optionally substituted $C_{1-6}$ alkyl group or optionally substituted $C_{6-14}$ aryl group. As substituent in the optionally substituted $C_{1-20}$ hydrocarbon residue, mention is made of (1) halogen, (2) nitro, (3) cyano, (4) an optionally substituted amino, (5) an optionally substituted hydroxyl group, (6) an optionally substituted carbamoyl, (7) an optionally substituted carboxyl, (8) an optionally substituted alkenyl, (9) acyl, (10) a group of the formula: —S(O)t—R$^{20}$ (wherein t denotes an integer of 0 to 2, and $R^6$ is a hydrogen atom or an optionally substituted hydrocarbon residue.) As the preferable example of optionally substituted homo-cyclic group, mention is made of an optionally substituted $C_{6-14}$ aryl group.

The substituents in the optionally substituted homo-cyclic group, mention is made of (1) halogen, (2) nitro, (3) an optionally substituted hydroxyl group, (4) a group of the formula: —S(O)t-$R^{20}$, wherein t denotes an integer of 0 to 2, and $R^{20}$ is a hydrogen atom or an optionally substituted hydrocarbon residue, or a $C_{1-10}$ hydrocarbon residue.

As the preferable example of the heterocyclic group in the optionally substituted heterocyclic group, mention is made of an optionally substituted 5- to 8-membered heterocyclic group, especially an optionally substituted 3- to 5-membered heterocyclic group having at least one nitrogen atom in a ring.

Preferred examples of the substituent to the heterocyclic group are (1) halogen, (2) nitro, (3) an optionally substituted hydroxyl group, (4) a group of the formula: -S(O)t-$R^{20}$ (wherein t denotes an integer of 0 to 2, and $R^{20}$ is a hydrogen atom or an optionally substituted hydrocarbon residue.), (5) an optionally substituted amino, or (6) a $C_{1-10}$ hydrocarbon residue.

In the formula (X), n is preferably 1.

In the above definitions, as the examples of halogen, mention is made of fluorine, chlorine, bromine, iodine.

As examples of $C_{1-6}$ alkyl, mention is made of methyl, ethyl, n-propyl, isopropyl, n-butyl, isobutyl, s-butyl, t-butyl, pentyl, isopentyl, neopentyl, hexyl.

$C_{1-4}$ alkyl is exemplified by methyl, ethyl, n-propyl, isopropyl, n-butyl, isobutyl, t-butyl. $C_{1-3}$ alkyl is exemplified by methyl, ethyl, n-propyl, isopropyl.

As examples of $C_{2-10}$ alkenyl, mention is made of vinyl, allyl, 2-methylallyl, isopropenyl, 2-butenyl, 3-butenyl, butadienyl, hexatrienyl, 3-octenyl. Examples of $C_{2-6}$ alkenyl are vinyl, allyl, isopropnyl, butenyl and hexatrienyl. Examples of $C_{2-4}$ alkenyl are vinyl, allyl, isopropenyl and butenyl.

As example of the $C_{2-10}$ alkynyl, mention is made of ethyl, 1-propynyl, 2-propynyl, propargyl, and 3-hexynyl. $C_{2-6}$ alkynyl and $C_{2-4}$ alkynyl is exemplified by ethynyl, 1-propynyl, 2-propynyl. $C_{3-10}$ cycloalkyl is exemplified by cyclopropyl, cyclobutyl, cyclopentyl, cyclohexyl, cycloheptyl, cyclooctyl, cyclononyl. $C_{3-8}$ cycloalkyl is exemplified by cyclopropyl, cyclobutyl, cyclopentyl, cyclohexyl, cycloheptyl, cyclooctyl. $C_{3-7}$ cycloalkyl is exemplified by cyclopropyl, cyclobutyl, cyclopentyl, cyclohexyl, cycloheptyl. $C_{3-6}$ cycloalkyl is exemplified by cyclopropyl, cyclobutyl, cyclopentyl, cyclohexyl.

Examples of $C_{3-7}$ cyclooclkenyl are cyclopropenyl, cyclobutenyl, cyclopentenyl, cyclohexenyl, cyclohexenyl, and examples of $C_{5-7}$ cycloalkenyl are cyclopentyl, cyclohexenyl.

$C_{6-14}$ aryl is exemplified by phenyl, naphthyl, anthryl, phenanthryl, acenaphthyl, anthracenyl. Examples of $C_{6-10}$ aryl are phenyl and naphthyl. Especially phenyl is most preferable.

$C_{7-20}$ aralkyl are $C_{7-19}$ aralkyl are exemplified by benzyl and phenethyl, benzhydryl, trithyl. $C_{7-15}$ aralkyl are benzyl, phenethyl, benzhydryl. Examples of $C_{7-11}$ aralkyl and $C_{7-10}$ aralkyl are benzyl, α-methylkenyl and phenethyl.

$C_{1-6}$ alkoxy is exemplified by methoxy, ethoxy, propoxy, isopropoxy, n-butoxy, isobutoxy, s-butoxy, t-butoxy, pentyloxy, isopentyloxy, neopentyloxy, hexyloxy, $C_{1-4}$ alkoxy is exemplified by methoxy, ethoxy, propoxy, isopropoxy, n-butoxy, isobutoxy, s-butoxy, t-butoxy. $C_{1-3}$ alkoxy is exemplified by methoxy, ethoxy, propoxy, isopropoxy.

$C_{1-6}$ acyl is exemplified by a $C_{1-6}$ alkanoyl group of the formula: —CO—$R^{25}$, wherein $R^{25}$ is hydrogen, methyl, ethyl, propyl, isopropyl, n-butyl, isobutyl, s-butyl, t-butyl, pentyl.

$C_{1-4}$ acyl is exemplified by a $C_{1-4}$ alkanoyl of the formula: —CO—$R^{25'}$, wherein $R^{25'}$ is hydrogen, methyl, ethyl, propyl, isopropyl.

Preferable five to seven-membered heterocyclic groups which contain 1 to 4 heteroatoms of oxygen, sulfur or nitrogen are exemplified by thienyl, furyl, pyrrolyl, pyrazolyl, thiazolyl, isothiazolyl, oxazolyl, isoxazolyl, imidazolyl, triazolyl, tetrazolyl, furazanyl, tetrahydrofuryl, pyridyl, pyrimidinyl, pyridazynyl, oxadiazolyl, tetrahydropyranyl, morpholinyl, thiomorpholinyl, pyrrolidinyl, pyrrolinyl, pyrazolidinyl, pyrazolinyl, imidazolidinyl, imidazolinyl, imidazolyl, 1,2,3-triazinyl, 1,2,3-triazolidinyl, 1,2,3-triazolyl, 1,2,3,4-tetrazolyl, piperidinyl, piperazinyl, hexamethyleneaminyl, oxazolidinyl or thiazolidinyl. As more preferable heterocyclic groups, mention is made of 5 to 6 membered heterocyclic groups. In particular, pyrrolidinyl, pyrazolinyl, pyrazolyl, piperidinyl, piperazinyl, morpholinyl and thiomorpholinyl are preferable.

The present compound [I], [X] and its salt can be produced easily by per se known methods, as exemplified by the following procedures.

In the following production methods, $R^I$ denotes a hydrogen atom or $R^a$, $R^{II}$ denotes $R^I$ or $R^b$, $R^{III}$ denotes $R^2$ or $R^c$, $R^{IV}$ denotes $R^3$ or $R^a$, $R^V$ denotes $R^4$ or $R^g$, respectively.

As the leaving group shown by X, mention is made of, for example, a group which is potentially substituted by a nucleophilic reagent such as a hydrocarbon residue having a hetero atom (e.g. an oxygen atom, a sulfur atom, a nitrogen atom) being negatively charged. The preferable examples of the leaving group include halogen, e.g. iodine, bromine chlorine, alkanoyloxy, e.g. acetoxy, alkylsulfonyloxy, e.g. methanesulfonyloxy, alkyl-arylsulfonyloxy, e.g. p-toluenesulfonyloxy.

Production Method 1:

To a solution of 3-halogenated aniline derivative (i) is added an equivalent mole to a small excess amount of ethoxymethylene melonic acid diethylester, the mixture is stirred for one to 4 hours at a temperature of 100° C. to 150° C. to give an additive form (ii). The additive form (ii) is dissolved stepwise in an appropriate solvent, e.g. polyphosphoric acid, polyphosphoric acid ester (PPE), Dowtherm, the mixture is stirred at room temperature to heating to give a quinoline derivative (iii). The derivative (iii) is dissolved in an appropriate solvent, i.e. one which does not adversely affect the reaction, e.g. dimethylformamide, dichloromethane, tetrahydrofuran, ethylether, dioxane, aceton.

To the solution is added one equivalen to a small excess amount of a base, e.g. potassium carbonate, triethylamine, sodium hydrogen, one equivalent to excess amount of halogens alkyl derivative, e.g. methyl iodide, propyl iodide, benzyl iodide, and the mixture is stirred at a temperature of 0° C. to 80° C. to give a quinoline derivative (iv).

Thus obtained derivative (iv), e.g. the present compound (II), or its salt and an equivalent mole to a small excess amount (about 3 mole) of an aryl boric acid derivative, i.e. $R^{III}$—B(OH)$_2$, e.g. $R^2$—B(OH)$_2$, are reacted to give the compound (Ia) shown in the following Scheme 1. The reaction is carried out in an appropriate solvent which does not adversely affect the reaction. As the solvent, mention is made of dimethoxyethane, tetrahydrofuran, dioxane, benzene, toluene, ethylether, dimethylformamide, dimethylacetamide and ethanol. This reaction is carried out in the presence of a base. As the base, mention is made of inorganic base such as sodium carbonate, sodium hydrogencarbonate, potassium carbonate, potassium hydrogencarbonate, sodium hydroxide, potassium hydroxide, thallium carbonate or an organic base such as triethylamine. In order to proceed the reaction smoothly, a catalytic amount of palladium derivative, e.g. tetrakistriphenylphosphine palladium, may be added to the reaction system. It is preferable to carry out the reaction in a stream of an inert gas, e.g. argon gas, nitrogen gas. The reaction is carried out at room temperature to about 150° C. and it is preferable to carry out the reaction under refluxing. The reaction time is about 1 to 12 hours. This reaction gives the desired product (Ia).

The foregoing methods are shown in Scheme 1. In Scheme 1, Et denotes ethyl, Y denote halogen, whose examples are the same as above, and the other groups have the same meaning as defined above.

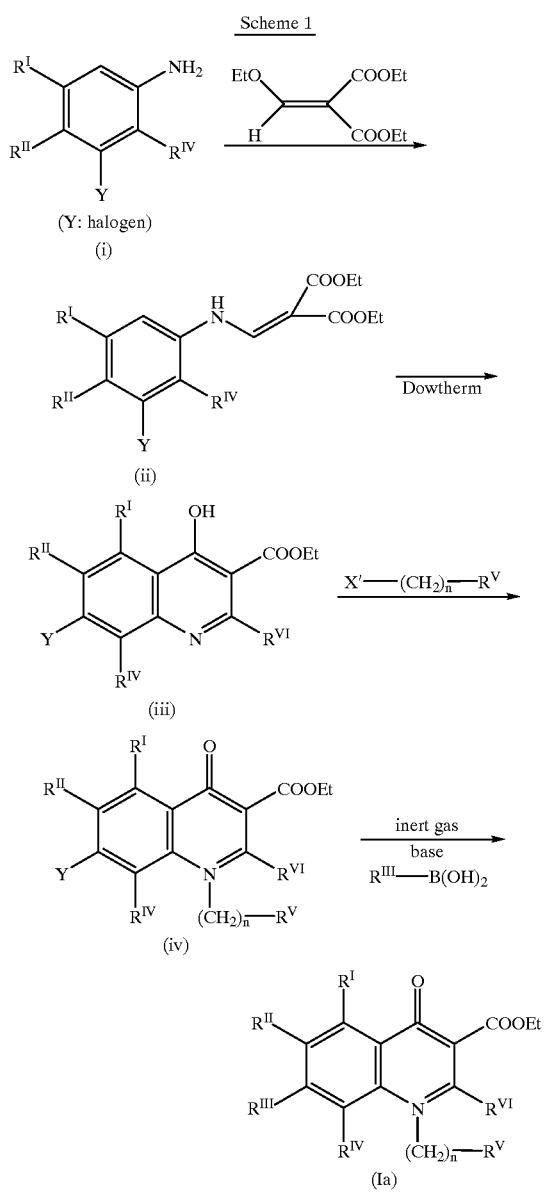

Production Method 2:

Exchange the group at 6-position:

The compound (v) is stirred together with N-bromosuccinimide (NBS) in an appropriate solvent, e.g. halogenated hydrocarbons such as carbon tetrachloride and chloroform in the presence of α, α'-azobisisobutyronitrile (AIBN), at temperatures ranging from about 30 to 100° C. for 0.5 to 6 hours to give a compound (vi).

The compound (vi), e.g. the present compound (III), or its salt is reacted with about equivalent mole of an amine of the formula: $R^{1'}13$ H, e.g. the compound shown by the formula: $HNR^5R^6$, to produce the compound (Ib). The reaction is carried out in an appropriate solvent which does not adversely affect the reaction. As the solvent, mention is made of amides such as dimethylformamide and dimethylacetamide, nitrils such as acetonitrile, alcohols such as ethanol, furthermore in the reaction dimethoxyethane, tetrahydrofuran, dioxane, dichloromethane, acetonitrile, acetone, ethyl acetate can be used as a solvent. The reaction is carried out in the presence of a base such as tertiary organic amine, e.g. triethylamine, trimethylamine, diisopropylethylamine, N-methylmorpholine. The reaction temperature is normally about 10 to 100° C. The reaction time is about 1 to 10 hours. It is preferable to carry out the reaction under stirring.

This reaction gives the compound (Ib). The production method 2 described above is shown in Scheme 2: In Scheme 2, $R^{1'}$ denotes an optionally substituted amino group, Z is a leaving group X. Other groups have the same meaning as defined above.

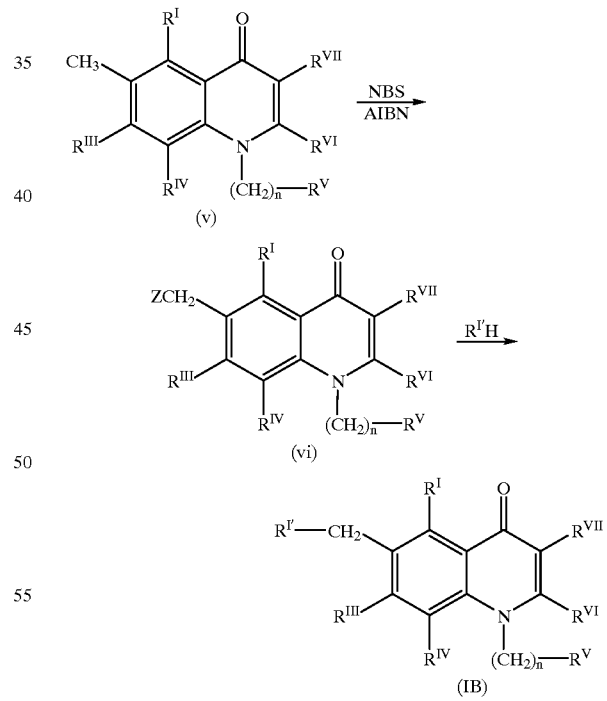

Production Method 3

An anthranilic acid derivative (vii) is stirred at temperatures ranging from about 30 to 110° C. together with an equivalent or an excess amount of triphosgene in an appropriate solvent, e.g. ethers such as tetrahydrofuran and 1,4-dioxane, to give an isatoic acid anhydride derivative (viii). Then, a halogenated derivative is stirred at temperatures ranging from about 40 to 130° C. in an appropriate solvent, e.g. ethers such as tetrahydrofuran and 1,4-dioxane, aromatic hydrocarbons such as benzene and toluene, amides such as N,N-dimethylformamide and N,N-dimethylacetamide, alkylsulfoxides such as dimethyl sulfoxide, in the presence of a base, e.g. alkali metal carbonate such as potassium carbonate, alkali metal hydride such as sodium hydride and potassium hydride, and alkali metal alkoxide such as potassium-butoxide, to give a substituted derivative (xi). The derivative (xi) is allowed to react with an equivalent or a little excess amount, e.g. about 1.1 to 1.5 equivalent, of a β-keto-acid ester derivative (xiv) relative to the compound at temperatures ranging from 40 to 110° C. in an appropriate solvent, e.g. ethers such as tetrahydrofuran and 1,4-dioxane, aromatic hydrocarbons such as benzene and toluene, amides such as N,N-dimethylformamide and N,N-dimethylacetamide, and alkyl sulfoxide such as dimethyl sulfoxide, in the presence of a base, e.g. alkali metal carbonate such as potassium carbonate, alkali metal hydride such as sodium hydride and potassium hydride, and alkali metal alkoxide such as potassium-butoxide, to give the compound (Ic). The foregoing production method 3 is shown in Scheme 3. In Scheme 3, Xa denotes a leaving group especially halogen, and $R^{g'}$ denotes an alkyl group. Other groups have the same meaning as defined above.

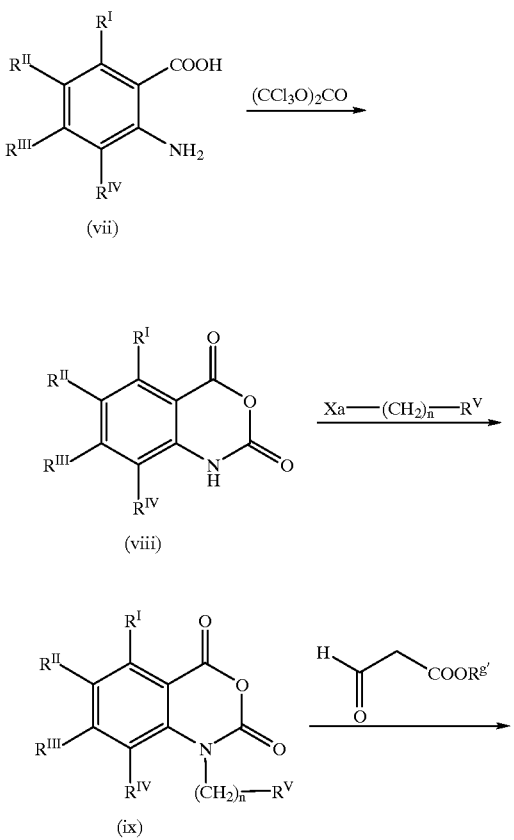

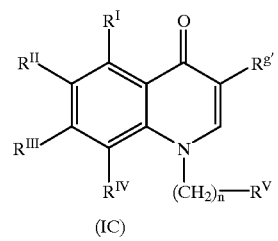

4. Other methods:

The substituents on the compound (I) can be converted to other substituents by er se known and conventional methods. Examples of the methods are shown below.

(i) The nitro group as the substituent can be converted to an amino group when the starting compound is dissolved in an appropriate solvent, e.g. ethanol, methanol, and (a) to the solution is added palladiumcarbon, and the mixture is reacted at room temperature for one to 12 hours under hydrogen atmosphere, or (b) to the solution is added iron powder and hydrochloric acid, and the mixture is reacted at room temperature for one to 12 hours.

(ii) The amino group can be converted to an acylated amino group by dissolving the starting compound in an appropriate solvent, e.g. tetrahydrofuran, dimethylsulfoxide, to the solution is added potassium carbonate, pyridine and triethylamine as a base and acid anhydride or acid halide. The mixture is reacted at a room temperature for one to 10 hours under stirring.

(iii) From an amino compound, a compound having an amino group is converted to alkenyl-amino compound. For example, the starting compound is dissolved in an appropriate solvent, e.g. acetic acid, dimethylformamide, dichloromethane, tetrahydrofuran, dioxane, acetonitrile, to the solution is added diazonizing agent, e.g. sodium nitrite, isoamyl nitrite, to the mixture is added palladium catalyst, e.g. bis(dibenzylideneacetone)palladium and one to excess equivalents of alkenyl derivative, and the mixture is stirred at room temperature to heating (about 80° C.) for one to 12 hours.

(iv) A carbon atom can be introduced to the amino group, for example, to the starting compound in an appropriate solvent, e.g. acetic acid, dimethylformamide, dichloromethane, tetrahydrofuran, dioxane, is added an acrylic acid derivative or oxirane derivative, e.g. epoxide compound. The mixture is stirred at 0 to 80° C. for 6 to 24 hours.

(v) A sulfur atom can be introduced to the amino group in the compound, for example, to the starting compound in an appropriate solvent, e.g. pyridine, dimethylformamide, dichloromethane, tetrahydrofuran, ethylether, dioxane, is added halide of sulfur compound. The mixture is stirred at 0 to 80° C. for 6 to 24 hours.

(vi) The substituent, formyl group, can be converted to methyl group by dissolving a starting compound in an appropriate solvent, e.g. tetrahydrofuran, and to the mixture is added an organic borane, derivative, e.g. dimethylsulfide borane, and the mixture is reacted at room temperature to heating under reflux for a several hours, e.g. one to 3 hours.

(vii) From methoxy derivative, actonyloxy derivative can be prepared by dissolving the starting material is dissolved in an appropriate solvent, e.g. dichloromethane, and to the solution is added one to excess equivalents of Lewis acid, e.g. aluminium chloride, and thiol compound or sulfide compound (e.g. dimethylsulfide), and the mixture is reacted at ice-cooling to room temperature for one to 10 hours, and then the obtained hydroxy derivative is dissolved in an appropriate solvent, e.g. dimethylformamide, to the solution is added a base, e.g. sodium hydroxide or potassium carbonate, and an alkyl halide. The mixture is reacted at a room temperature for one to 12 hours.

(viii) A methoxy group can be changed to isopropoxy is dissolving the starting material in an appropriate solvent, e.g. dichloromethane, to the solution is added one to excess equivalents of Lewis acid, e.g. aluminum chloride, and thiol compound or sulfide compound, e.g. dimethylsulfide, and the mixture is reacted at room temperature to ice-cooling for one to 10 hours.

(ix) An aminocarbonyl group can be introduced by dissolving a starting compound having halogen atom in an appropriate solvent, e.g. dimethoxyethane, to the solution is added arylborric acid derivative, a base, e.g. sodium carbonate, a palladium compound e.g. tetrakis(triphenylphosphine)palladium(0), as a catalyst and the mixture is refluxed 1 to 6 hours.

(x) An alkylthio compound can be converted to an alkylsulfinyl compound or an alkylsulfonyl compound by reacting a starting compound with an oxidizing agent, e.g. metachloroperbenzoic acid, in an appropriate solvent, e.g. dichloromethane, at ice-cooling to heating. With vigorous heating or by treating with an excess amount of oxidizing agent, an alkylsulfonyl compound is obtained.

As salts of the compound (I) of this invention obtained thus above, physiologically acceptable acid addition salts are preferable. Examples of such salts include those with an inorganic acid, e.g. hydrochloric acid, hydrobromic acid, nitric acid, sulfuric acid and phosphoric acid, or those with an organic acid, e.g. formic acid, acetic acid, trifluoroacetic acid, fumaric acid, oxalic acid, tartaric acid, maleic acid, citric acid, succinic acid, malic acid, methanesulfonic acid, bezenesulfonic acid, and p-toluenesulfonic acid). Further, when the compound (I) of this invention has an acid group such as —COOH, the compound (I) may form a salt with an inorganic base, e.g. an alkali metal or alkaline earth metal such as sodium, potassium, calcium and magnesium; ammonia, or an organic base, e.g. trimethylamine, triethylamine, pyridine, picolin, ethanolamine, diethanolamine, triethanolamine, dicyclohexylamine and N,N'-dibenzylethylenediamine.

The compound (I) or salts thereof of the present invention produced thus above can be isolated and purified by conventional separating means such as recrystallization, distillation and chromatography. In the case where the compound (I) is produced in the free form, it can be converted to a salt thereof by a per se conventional means or a method analogous thereto. On the contrary, when it is obtained in the form of a salt, it can be converted to its free form or to any other salt.

In the case where the compound (I) or a salt thereof of the present invention is an optically active compound, it can be separated into d-compound and l-compound by means of a conventional optical resolution.

When the compound (X) forms a salt, the salt can be produced by a similar manner as described above.

Since the compounds (I) of this invention or its salt, hereinafter, it is sometimes abbreviated as "the present compound", have a GnRH antagonistic activity and are low in toxicity, and is stably absorbed through oral administration and shows GnRH antagonistic activity over a long time, they can be safely used for the therapy of male hormone or female hormone dependent diseases as well as the therapy of diseases caused by excess secretion of these hormones, in mammals, e.g. human, monkey, cow, horse, dog, cat, rabbit, rat and mouse, suppressing the secretion of gonadotropic hormone by the action of GnRH receptor antagonistic action. More specifically, the present compound are effective as a prophylactic or therapeutic agent for the prevention or treatment of several hormone dependent diseases, for example, a sex hormone dependent cancer, e.g. prostate cancer, cancer of the uterine cervix, breast cancer, pituitary adenoma, benign prostatic hypertrophy, myoma of the uterus, endometriosis, precocious puberty, amenorrhea, premenstrual syndrome, polycystic ovary syndrome and acne vulgaris. And, the present compound are also effective as a fertility controlling agent in both sexes, e.g. pregnancy controlling agents and menstrual cycle controlling agents. The present compound can be further used as a contraceptive of male or female and, as an ovulation-inducing agent of female. The present compound can be used as an infertility treating agent by using a rebound effect owing to a stoppage of administration thereof. Further, the present compound are useful as modulating estrous cycles in animals in the field of animal husbandry, and as an agent for improving the quality of edible meat or promoting the growth of animals. The present compound are also useful as an agent for promoting spawning in fish. While the present compound can be used singly, they can also effectively be used by administering in combination with a steroidal or non-steroidal antiandrogenic agent. The present compound can be used for the suppressing a passing ascent of testosterone concentration in plasma, the ascent which occurs in administration of GnRH super antagonist such as leuprorelin acetate. The present compound can effectively be used by administering in combination with a chemotherapeutic agent for cancer. In treatment of prostate cancer, examples of the chemotyerapeutic agent include Ifosfamide, UFT, Adriamycin, Peplomycin, Cisplatin and the like. In treatment of breast cancer, examples of the chemotherapeutic agent include Cyclophohamide, 5-FU-, UFT, Methotrexate, Adriamycin, Mitomycin C, Mitoxantrone and the like.

When the present compound is employed, in the field of animal husbandry or fisheries, as prophylactic and therapeutic agents of the above-mentioned diseases, it can be administered orally or non-orally in accordance with per se known means. For example, it can be mixed with a pharmaceutically acceptable carrier and administered orally as a solid preparation such as tablet, capsule, granule or powder, or non-orally as intravenous, subcutaneous or intramuscular injection, or as suppository or sublingually administrable tablet. Further, it can be sublingually, subcutaneously or intramuscularly administered as a prolonged release formulation such as sublingually administrable tablets, or microcapsules. The dosage can vary with, e.g. the degree of affliction, age, sex, body weight and difference of sensitivity of the subject to be treated, the time and intervals of administration, properties, dosage forms and kinds of the medicinal preparation, and kinds of the effective components, and it ranges usually, though not specifically limited to, from about 0.1 to 30 mg, preferably from about 0.1 to 3 mg, more preferably from about 0.1 to 1 mg, relative to 1 kg body weight of mammals, which is administered usually once daily or by 2 to 4 divided dosages. The daily dose when used in the field of animal husbandry or fishery varies with the conditions analogous to those mentioned above, it ranges, relative to 1 kg body weight of the subject animal or fish, from about 0.01 to 5 mg, preferably from about 0.03 to 3 mg, once daily or by 2 to 3 divided dosages.

As the above-mentioned pharmaceutically acceptable carriers, conventional various organic or inorganic carriers are used, and they can be incorporated as excipients, lubricants, binders, disintegrants in solid compositions; and as solvents, solubilisers, suspending agents, isotonizing agents, buffering agents and pain-easing agents in liquid and solid compositions. And, depending on necessity, further additives such as preservatives, anti-oxidants, coloring agents and sweeteners can also be used.

Preferable examples of the above-mentioned excipients include lactose, sugar, D-mannito, starch, crystalline cellulose and more volatile silicon dioxide. Preferable examples of the above-mentioned lubricants include magnesium stearate, calcium stearate, talc and colloid silica. Preferable examples of the above-mentioned binders include crystalline cellulose, sugar, D-mannitol, dextrin, hydroxypropyl cellulose, hydroxymethyl cellulose and polyvinyl pyrrolidone. Preferable examples of the above-mentioned disintegrants include starch, carboxymethyl cellulose, carboxymethyl cellulose calcium, cross carmelose sodium, cross carmelose sodium and carboxymethyl starch sodium. Preferable examples of the above-mentioned solvents include water for injection, alcohol, propylene glycol, macrogol, sesame oil and corn oil. Preferable examples of the above-mentioned solubilizers include polyethylene glycol, propylene glycol, D-mannitol, benzyl benzoate, ethanol, trisaminomethane, cholesterol, triethanolamine, sodium carbonate and sodium citrate. Preferable examples of the above-mentioned suspending agents include surfactants such as stearyl triethanolamine, sodium lauryl sulfate, lauryl aminopropionic acid, lecithin, benzalkonium chloride, benzetonium chloride and monostearic glyceryl ester; and hydrophilic polymers such as polyvinyl alcohol, polyvinyl pyrrolidone, sodium carboxymethyl cellulose, methyl cellulose, hydroxymethyl cellulose, hydroxyethyl cellulose and hydroxypropyl cellulose. Preferable examples of the above-mentioned isotonizing agents include sodium chloride, glycerin and D-mannitol. Preferable examples of the above-mentioned buffering agents include buffer solutions such as phosphate, acetate, carbonate and citrate. Preferable examples of the above-mentioned pain-easing agents include benzyl alcohol. Preferable examples of the above-mentioned preservatives include para-hydroxybenzoic acid esters, chlorobutanol, benzyl alcohol, phenethyl alcohol, dehydroacetic acid and sorbic acid. Preferable examples of the above-mentioned anti-oxidants include sulfite and ascorbic acid.

To the present compound, are added, for example, a suspending agent, a solubilizer, a stabilizer, an isotonizing agent and a preservative, then the mixture is formulated, in accordance with a per se known method, into an intravenous, subcutaneous or intramuscular injection. These injections can be processed into lyophilized preparations, when necessary, by a per se known method.

Examples of the above-mentioned pharmaceutical composition are oral agents (e.g. diluted powders, granules, capsules and tablets), injections, dropping injections, external agents (e.g. transnasal preparations, percutaneous preparations, etc.), ointments (e.g. rectal ointment, vaginal ointment, etc.) and the like.

Such pharmaceutical compositions can be manufactured by a per se known method commonly used in preparing pharmaceutical compositions.

The present compound can be made into injections either in a form of an aqueous injection together with dispersing agents [e.g. Tween 80 (Atlas Powder, U.S.A.), HCO 80 (Nikko Chemicals, Japan), polyethylene glycol, carboxymethylcellulose, sodium alginate, etc.], preservatives (e.g. methyl paraben, propyl paraben, benzyl alcohol, etc.), isotonizing agents (e.g. sodium chloride, mannitol, sorbitol, glucose, etc.) and the like or in a form of an oily injection by dissolving, suspending or emulsifying in plant oil (e.g. olive oil, sesame oil, cotton seed oil, corn oil, etc.), propylene glycol and the like.

In preparing a pharmaceutical composition for oral use, the present compound is molded by compressing, for example, with fillers (e.g. lactose, sucrose, starch, etc.), disintegrating agents (e.g. starch, calcium carbonate, etc.), binders (e.g. starch, gum arabic, carboxymethylcellulose,, polyvinylpyrrolidone, hydroxypropylcellulose, etc.) or lubricants (e.g. talc, magnesium stearate, polyethylene glycol 6000, etc.) and the like. If necessary, the present composition is coated by a per se known method with an object of masking the taste, as an enteric coating or for long-acting sustained refease. Examples of coating agent therefore are hydroxypropylmethylcellulose, ethylcellulose, hydroxymethylcellulose, hydroxypropylcellulose, polyoxyethylene glycol, Tween 80, pluronic F 68, cellulose acetate phthalate, hydroxypropylmethylcellulose phthalate, hydroxymethylcellulose acetate succinate, Eudragit (a copolymer of methacrylic acid with acrylic acid; manufactured by Rohm, Germany), red oxide of iron and the like. Subcoating layers may be provided between the enteric coating and the core according to per se known methods.

In preparing an external composition, the present compound is subjected to a per se known method to give a solid, semisolid or liquid agent for external use. For example, the solid preparation is manufactured as follows. The present compound as it is or after adding/mixing fillers (e.g. glycol, mannitol, starch, microcrystalline cullulose, etc.), thickeners (e.g. natural gums, cellulose derivatives, acrylic acid polymers, etc.) and the like thereto/therewith is made into a powdery composition. With respect to the liquid composition, an oily or aqueous suspension is manufactured by the manner nearly the same as in the case of the injection. In the case of a semisolid composition, the preferred one is an aqueous or oily gel or an ointment. Each of them may be compounded with a pH adjusting agent (e.g. carbonic acid, phosphoric acid, citric acid, hydrochloric acid, sodium hydroxide, etc.), an antiseptic agent (e.g. p-hydroxybenzoates, chlorobutanol, benzalkonium chloride, etc.) and the like.

In the manufacture of an ointment for example, the present compound can be made into an oily or an aqueous solid, semisolid or liquid ointment. Examples of the oily base material applicable in the above-mentioned composition are glycerides of higher fatty acids [e.g. cacao butter, Witepsols (manufactured by Dynamite-Nobel), etc.], medium fatty acids [e.g. Miglyols (manufactured by Dynamite-Nobel), etc.] and plant oil (e.g. sesame oil, soybean oil, cotton seed oil, etc.) and the like. Examples of the aqueous base material are polyethylene glycols and propylene glycol and those of the base material for aqueous gel are natural gums, cellulose derivatives, vinyl polymers, acrylic acid polymers, etc.

As the compound (X) or its salt has the same activity as the compound (I) or its salt, the compound (X) can be used in the same amount and the same administration method for the same purpose of the compound (I).

By way of the following Reference Examples and Working Examples the present invention will be described more specifically, but they are not intended to limit the scope of this invention thereto.

$^1$H-NMR spectra were taken with JEOL LAMBDA300 (300MHz) type spectrometer or the Brucker AM 500 (500 MHz) type spectrometer, employing tetramethylsilane as the internal standard. All delta values were expressed in ppm.

The symbols used in the present specification have the following meanings:

s: singlet, d: doublet, t: triplet, dt: double triplet, m: multiplet, br: broad

REFERENCE EXAMPLE 1

Production of (3-bromo-4-methylphenyl) aminomethylenemalonic acid diethylester:

To 3-bromo-4-methylaniline (20.0 g, 107.5 mmol) was added ethoxymethylenemalonic acid diethylester (23.2 g, 107.5 mmol), and the mixture was stirred for 2 hours at 120° C. After cooling, the reaction mixture was concentrated to dryness, and recrystallized from ether-n-hexane to give colorless crystals (29.0 g, 76%).

m.p. 66–67° C.

REFERENCE EXAMPLE 2

Production of 4-hydroxy-6-methyl-7-bromoquinoline-3-carboxylic acid ethylester:

To Dowthern (50 ml) was added stepwise the compound (5.0 g, 14.04 mmol) obtained in Reference Example 1 under stirring at 250° C. After stirring at the same temperature for 50 minutes, the reaction mixture was cooled. To the mixture was added ether, and the precipitated solid was recovered by filtration and washed again with ether. Thus obtained powder was recrystallized from ethanol to give colorless crystals (2.89 g, 66%). m.p. more than 250° C.

REFERENCE EXAMPLE 3

Production of 1,4-dihydro-1-(2,6-difluorobenzyl)-6-methyl-7-bromo-4-oxoquinoline-3-carboxylic acid ethylester:

To a solution of the compound (2.89 g, 9.32 mmol) obtained in Reference Example 2 in dimethylformamide (120 ml) were added potassium carbonate (1.54 g, 11.18 mmol) and potassium iodide (0.773 g, 4.66 mmol), and to the mixture was added dropwise 2,6-difluorobenzyl chloride (1.82 g, 11.18 mmol) under stirring.

The reaction mixture was stirred for 2 hours at 50° C., and concentrated. Thus obtained residue was partitioned between dichloromethane and water. The aqueous layer was extracted with dichloromethane, extracts were combined, washed with an aqueous sodium chloride solution, dried with MgSO$_4$, and the solvent was distilled off under reduced pressure.

Thus obtained residue was purified by silica gel chromatography to give colorless solid, and recrystallized from chloroform-ether to give colorless crystals (3.0 g, 73%).

m.p. 199–200° C.

EXAMPLE 1

Production of 1,4-dihydro-1-(2,6-difluorobenzyl)-6-methyl-7-(4-propionylaminophenyl)-4-oxoquinoline-3-carboxylic acid ethyl ester:

To a solution of the compound (1.0 g, 2.29 mmol) obtained in Reference Example 3 in dimethoxyethane (50 ml) were added 2M aqueous sodium carbonate solution (5.73 ml, 11.45 mmol), 4-propionylaminophenyl boric acid (0.487 g, 2.52 mmol) and tetrakistriphenylphosphinepalladium(O) (0.266 g, 0.23 mmol), and the mixture was refluxed under heating for 5 hours. After cooling, the reaction mixture was partitioned between dichloromethane and water. The aqueous layer was extracted between dichloromethane, extracts were combined, washed with an aqueous sodoium chloride solution, dried with MgSO$_4$, and the solvent was distilled off under reduced pressure.

Thus obtained residue was purified by silica gel chromatography to give colorless solid, and recrystallized from chloroform-ether to give colorless crystals (0.72 g, 62%).

m.p. 263–264° C.

EXAMPLE 2

Production of 6-bromomethyl-1,4-dihydro-1-(2,6-difluorobenzyl)-7-(4-propionylaminophenyl)-4-oxoquinoline-3-carboxylic acid ethyl ester:

The compound (0.70 g, 1.39 mmol) obtained in Example 1, N-bromosuccinimide (0.26 g, 1.46 mmol) and α,α'-azobisisobutyronitrile (0.046 g, 0.18 mmol) was added to 1,2-dichloroethane (150 ml). The mixture was refluxed under heating for 5 hours. After cooling, the insolubles were removed off by filtration, and the filtrate was diluted by chloroform.

The organic layer was washed with an aqueous sodium chloride solution, dried with MgSO$_4$, and the solvent was distilled off under reduced pressure.

Thus obtained residue was purified by silica gel chromatography to give colorless solid (0.58 g, 72%), and recrystallized from chloroform-ether to give colorless crystals (0.443 g, 55%).

m.p. 251–253° C.

EXAMPLE 3

Production of 6-(N-benzyl-N-methylaminomethyl)-1,4-dihydro-1-(2,6-difluorobenzyl)-7-(4-propionylaminophenyl)-4-oxoquinoline-3-carboxylic acid ethyl ester hydrochloride:

The compound (0.42 g, 0.72 mmol) obtained in Example 2 was dissolved in dimethylformamide (80 ml), and to the solution were added ethyldiisopropylamine (0.112 g, 0.86 mmol) and N-benzyl-N-methylamine (0.105 g, 0.86 mmol). The mixture was stirred for 2.5 hours at room temperature, and concentrated. Thus obtained residue was partitioned between dichloromethane and saturated aqueous sodium bicarbonate. The aqueous layer was extracted with chloroform, extracts and the organic layer were combined, dried with MgSO$_4$, and the solvent was distilled off under reduced pressure. Thus obtained residue was purified by silica gel chromatography to give colorless oily product (0.46 g, 100%). To a solution of the oily product (0.20 g) in dichloromethane (20 ml) was added 1N hydrogen chloride in ether (0.04 ml), and the mixture was stirred for 10 minutes at the same temperature. The reaction mixture was concentrated under reduced pressure, and thus obtained residue was recrystallized from ethyl acetate-ethanol to give white crystals of the titled compound as hydrochloride (0.138 g, 66%).

m.p. 165–168° (hydrochloride)

The compounds shown in the above Examples are listed in the following Table 1.

TABLE 1

[Chemical structure: quinoline derivative with R¹ substituent, C₂H₅—CO—NH— group on phenyl, COO—C₂H₅ ester, and N-CH₂-(2,6-difluorophenyl) group]

| Example No. | R¹ |
|---|---|
| 1 | methyl |
| 2 | bromomethyl |
| 3 | N-benzyl-N-methylaminomethyl |

EXAMPLE 4

Using the compound produced in Example 3, lactose (165 mg), cornstarch (25 mg), polyvinyl alcohol (4 mg) and magnesium stearate (1 mg), tablets are prepared by a conventional method.

EXAMPLE 5

The compound produced in Example 3 is dissolved in distilled water for injection to make the whole volume 100 ml. This solution is subjected to sterilized filtration through 0.22 μm membrane filter (manufactured by Sumitomo Electric Industries, Ltd. or Zartolius Inc.), 2 ml each of which is divided into sterilized vials, followed by lyophilization to prepare a lyophilized injectable composition of 100 mg/vial.

EXAMPLE 6

| | |
|---|---|
| (1) Compound produced in Example 3 | 5 g |
| (2) Lactose.crystalline cellulose (granules) | 330 g |
| (3) D-mannitol | 29 g |
| (4) Low-substituted hydroxypropyl cellulose | 20 g |
| (5) Talc | 25 g |
| (6) Hydroxypropyl cellulose | 50 g |
| (7) Aspartalne | 3 g |
| (B) Dipotassium glycyrrhetinate | 3 g |
| (9) Hydroxypropylmethyl cellulose 2910 | 30 g |
| (10) Titanium oxide | 3.5 g |
| (11) Yellow iron sesquioxide | 0.5 g |
| (12) Light silicic acid anhydride | 1 g |

In refined water are suspended or dissolved (1), (3), (4), (5), (7) and (8). The nuclear granule of (2) is coated with the suspension or solution to prepare raw fine granules, which are coated with (9)–(11) to prepare coated fine granules, which are mixed with (12), to give 500 g of fine granules containing 1% of the compound produced in Example 3. 500 mg each of thus-prepared fine granules is packed.

TEST EXAMPLE 1

(1) Preparation of $^{125}$I-leuprorelin

Ten μl of a 3×10 M aqueous solution of leuprorelin and 10 μl of 0.01 mg/ml lactoperoxidase in 0.1M HEPES buffer (pH 7.4) were taken into a tube, to which was added 10 μl [37MBq in 0.1M HEPES buffer (pH 7.4)] of an Na$^{125}$I solution. The mixture was stirred, to which was added 10 μl of 0.001% $H_2O_2$, then reaction was allowed to proceed for 20 minutes at room temperature. To the reaction mixture was added 700 μl of a 0.05% TFA solution to stop the reaction. The product was purified by means of reversed phase HPLC. Conditions of HPLC are as follows. $^{125}$I-leuprorelin was eluted at a retention time of 26 to 27 minutes.

Column: TSK gel ODS-80 ™ CTR (4.6 mm×10 cm)

Eluent:

Solvent A (0.05% TFA)

Solvent B (40%$CH_3CN$—0.05% TFA)

0 minute (100% Solvent A)–3 minutes (100% Solvent A)–7 minutes (50% Solvent A+50% Solvent B)–40 minutes (100% Solvent B)

Elution temp.: room temperature

Flow rate : 1 ml/min.

(2) Preparation of membrane fraction of CHO (Chinese Hamster Ovary) cells containing human GnRH receptors CHO cells ($10^9$) expressing human GnRH receptors were suspended in a phosphate-buffered saline supplemented with 5mM EDTA (PBS-EDTA). The suspension was subjected to centrifugal separation for 5 minutes at 100×g. To the pellet of cells was added 10 ml of a homogenate buffer for cells (10 mM $NaHCO_3$, 5 mM EDTA ethylenediamine tetraacetate), pH 7.5), which was homogenated by using a Polytron homogenizer. Centrifugal separation was conducted for 15 minutes at 400×g. The supernatant was taken into an ultracentrifugal tube, which was subjected to centrifuge for one hour at 100,000×g to give precipitate of the membrane fraction. The precipitate was suspended in 2 ml of the assay buffer (25 mM Tris-HCl, 1 mM EDTA , 0.1% BSA (bovine serum albumin), 0.25 mM PMSF, 1 μg/ml pepstatin, 20 μg/ml leupeptin, 100 μg/ml phosphoramidon, 0.03% sodium azide, pH 7.5), which was centrifuged for one hour at 100,000×g. The membrane fraction recovered as precipitate was again suspended in 20 ml of the assay buffer, which was distributed to vials and stored at −80° C. until used.

(3) Determination of inhibitory rate of $^{125}$I-leuprorelin binding

Membrane fraction of CHO cells expressing human GnRH receptors prepared in the above (2) was diluted with an assay buffer to 200 μg/ml and 188 μl each was distributed into tubes. 2 μl of 2 mM of the compound dissolved in 60% DMSO and 10 μl of 38 nM $^{125}$I-leuprorelin were added simultaneously to the CHO cell membrane fraction expressing human GnRH receptors. For determining the amount of maximum binding, a solution for reaction supplemented with 2 μl of 60% DMSO and 10 μl of 38 nM $^{125}$I-leuprorelin was prepared. And, for determining the amount of non-specific binding, a solution for reaction supplemented with 2 μl of 100 μM leuprorelin dissolved in 60% DMSO and 10 μl of 38nM $^{125}$I-leuprorelin were also prepared simultaneously.

The reaction was allowed to proceed at 25° C. for 60 minutes. The reaction mixtures were respectively subjected to filtration under sucking with Whatman glass filter (GF-F) processed with polyethylenimine. After completing the filtration, radioactivity of the $^{125}$I-leuprorelin remaining on the filter paper was measured with a γ-counter.

By calculation of $$MB=(TB-SB)/(TB-NSB)\times 100$$

(TB: maximum binding radioactivity, SB: radioactivity obtained when a compound was added, NSB: non-specific binding ratio activity, the binding inhibitory rate (PMB) (%) of each test compound was determined. Besides, the inhibitory rates were determined by changing the concentrations of test compounds, and the concentration of a test compound inhibiting the (TB-NSB) by 50% i.e. the concentration of PMB=50%, ($IC_{50}$ value) was calculated by way of Hill plot.

The compound obtained in Examples 3 was subjected to the above measurement methods, and obtained $IC_{50}$ values shown in the following Table 2.

TABLE 2

| | $^{125}$I-leuprorelin binding inhibitory rate |
|---|---|
| Test compound | $IC_{50}$ value (nM) human GnRH receptor |
| Compound of Example 3 | 50 |

INDUSTRIAL APPLICABILITY

The gonadotropin-releasing hormone antagonistic agent of the present invention is stably absorbed through oral administration and shows GnRH antagonistic activity over a long time. Therefore, the present compound can be used as a prophylactic or therapeutic agent for the prevention or treatment of several hormone dependent diseases, for example, a sex hormone dependent cancer, e.g. prostatic cancer pituitary adenoma), cancer of the uterine cervix, breast cancer, prostatic hypertrophy, myoma of the uterus, endometriosis, precocious puberty, amenorrhea syndrome, polycystic ovary syndrome and acne vulgaris, or as a fertility controlling agent, e.g. a contraceptive agent, infertility treating agent, a menstruation controlling agent. Further, in the field of animal husbandry, the gonaolotropin-releasing hormone antagonistic agent of the present invention is effective as an agent of controlling oestrus in animals, improving the quality of edible meat, growth regulation of animals, and also a spawning-accelerating agent in the field of fisheries.

What we claim is:

1. A compound of the formula:

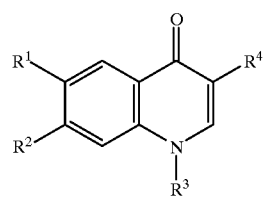

(I)

wherein $R^1$ is methyl $R^2$ is an acylaminoaryl group, $R^3$ is a halogenoaralkyl group, and $R^4$ is a carboxyl group which may optionally be esterified or amidated, or a salt thereof.

2. A compound according to claim 1, wherein $R^2$ is a $C_{1-6}$ acyl-amino-$C_{6-14}$ aryl group, $R^3$ is a halogeno-$C_{7-13}$ aralkyl group, and $R^4$ is a carboxyl group which may optionally be esterfied with $C_{1-6}$ alkyl.

3. A compound according to claim 1, wherein $R^2$ is propionylaminophenyl, and $R^3$ is diflurobenzyl.

* * * * *